United States Patent
Walker et al.

[11] 3,969,926
[45] July 20, 1976

[54] ALIGNMENT OF ULTRASONIC TRANSDUCER PROBE IN PULSE-ECHO TESTING

[75] Inventors: Philip A. Walker, Trumbull; Karl G. Walther, Ridgefield, both of Conn.

[73] Assignee: Krautkramer-Branson, Incorporated, Stratford, Conn.

[22] Filed: Mar. 27, 1975

[21] Appl. No.: 562,550

[52] U.S. Cl. .................................................. 73/67.8 S
[51] Int. Cl.² ............................................. G01N 29/04
[58] Field of Search............ 73/67.8 S, 67.7, 67.8 R, 73/67.9, 71.5 US

[56] References Cited
UNITED STATES PATENTS

| | | | |
|---|---|---|---|
| 3,678,736 | 7/1972 | May .............................. | 73/71.5 US |
| 3,690,311 | 9/1972 | Schorum et al. ................. | 73/67.8 S |
| 3,765,229 | 10/1973 | Spencer et al................... | 73/67.8 S |
| 3,857,052 | 12/1974 | Beller ............................. | 73/67.8 S |
| 3,898,838 | 8/1975 | Connelly.......................... | 73/67.8 S |

*Primary Examiner*—Herbert Goldstein
*Assistant Examiner*—Stephen A. Kreitman
*Attorney, Agent, or Firm*—Ervin B. Steinberg; Philip J. Feig

[57] ABSTRACT

This invention refers to an ultrasonic pulse-echo nondestructive test method and apparatus for causing the axis of an ultrasonic energy search beam path transmitted from an ultrasonic transducer probe to a workpiece to be maintained normal to an irregularly contoured workpiece entrant surface. Electrical circuit means measure and compare the echo signals reflected from the workpiece and cause the search probe to be positioned to maximize the amplitude of the received signals.

17 Claims, 9 Drawing Figures

ALIGNMENT OF ULTRASONIC TRANSDUCER PROBE IN PULSE-ECHO TESTING

BACKGROUND OF THE INVENTION

This invention refers to a material tester and more particularly to a novel and improved electrical system for directing an ultrasonic search unit of an ultrasonic nondestructive material tester, for example, over curved or sloped surfaces and the like.

The use of pulse-echo ultrasonic nondestructive test methods to inspect workpieces for flaws or defects is well-known in the prior art. It has been found that pulse-echo ultrasonic testing is best suited for large workpieces, whereby the search unit must scan the workpiece in such a manner as to ensure that the entire area of the workpiece is inspected. Normally, these scans are made along one axis with indexing of the probe along the other axis before the return scan is started. In the case where curved or contoured workpieces are tested, the workpiece is affixed to a rotatable worktable and an indexing search unit is used.

When testing workpieces by the pulse-echo ultrasonic test method, it is necessary generally to immerse the workpiece and the search unit in a liquid couplant material, such as water, for achieving good ultrasonic coupling.

In the prior art, devices capable of causing motion of the probe system along the scan axes include very complicated electrical tape programmed reading systems and digital and/or analog computers for deriving voltages to change the position of the test probe. The use of such complex systems is quite expensive.

Workpieces having a continuously changing slope are difficult to scan with pulse-echo ultrasonic testing. When testing these workpieces, a simultaneous change in the X and Y axis position is required to test for flaws and defects. Other types of workpieces which are difficult to test are curved wing surfaces of aircraft, turbine blades, and unevenly work railroad rails.

It is desired, therefore, to provide an automatic electrical control system which controls the axis position of a search unit to achieve scanning of irregularly shaped and curved workpieces.

SUMMARY OF THE INVENTION

The present invention concerns a pulse-echo ultrasonic test system in which the pulse-echo test transducer probe is aligned by suitable positioning means to cause the test beam axis to be at a predetermined angle to a selected workpiece surface. In a preferred embodiment, the beam is positioned normal to the entrant surface of the workpiece. In this manner the ultrasonic defect evaluation instrument receives echo signals which are at a maximum and the shape, location and identity of a defect within the workpiece can more accurately be identified. To this end, a preferred embodiment of the present invention discloses an arrangement wherein the test probe is supplemented by at least one laterally disposed alignment probe positioned at a fixed distance and at an angle with respect to the test probe, and which is energized cyclically for causing ultrasonic signals to be transmitted toward the workpiece and for receiving echo responsive signals therefrom. Alternatively, the test probe is straddled by at least a pair of laterally disposed alignment probes positioned at a fixed distance and at an angle with respect to the test probe. The alignment probes are energized cyclically for causing ultrasonic signals to be transmitted toward the workpiece and for receiving echo responsive signals therefrom. Any difference in the amplitude of the echo signals received by the respective alignment probes is indicative of the condition that the test beam axis of the test probe deviates from normal incidence upon the workpiece surface. The difference between the echo signals received by the alignment probes is used to position the test probe until the echo signals received by the alignment probes are of equal magnitude. The positioning of the test probe is done must suitably by servomechanism which is responsive to the difference of the heretofore stated echo signals.

The above stated arrangements are particularly useful for immersion testing of irregularly contoured workpieces. If the test probe is to be aligned along two perpendicular planes, two pairs of alignment probes are required. If each pair of probes is disposed in and is associated with one of the planes in which alignment is sought, it will be apparent that by means of the arrangement indicated heretofore, a completely automatic alignment procedure is achieved which ensures that the beam axis of the sonic energy propagated from the test probe is always normal to the selected workpiece surface and that such alignment can be done completely automatically and at predetermined intervals by suitably operated timing and gating means.

A principal object of the present invention, therefore, is the provision of a control circuit for an ultrasonic search unit for achieving scanning of irregularly shaped workpieces.

Another important object of the present invention is the provision of an ultrasonic pulse-echo test apparatus particularly suited for immersion testing in which a servomechanism system is coupled to the test probe for properly aligning the ultrasonic test probe with respect to the entrant surface or some other selected surface of the workpiece.

A further object of the present invention is the provision of a pulse-echo ultrasonic test apparatus utilizing alignment probes in conjunction wtih a test probe for producing signals indicative of the alignment or misalignment of the search unit relative to a selected workpiece surface, particularly signals indicative of the deviation of the search beam axis from being normal to such surface, and means for operating positioning means responsive to such signals.

Other and furthr objects of the present invention will become more clearly apparent from the following description when taken in conjunction with the accompanying drawings.

DETAILED DESCRIPTION OF THE INVENTION

Figure 1:
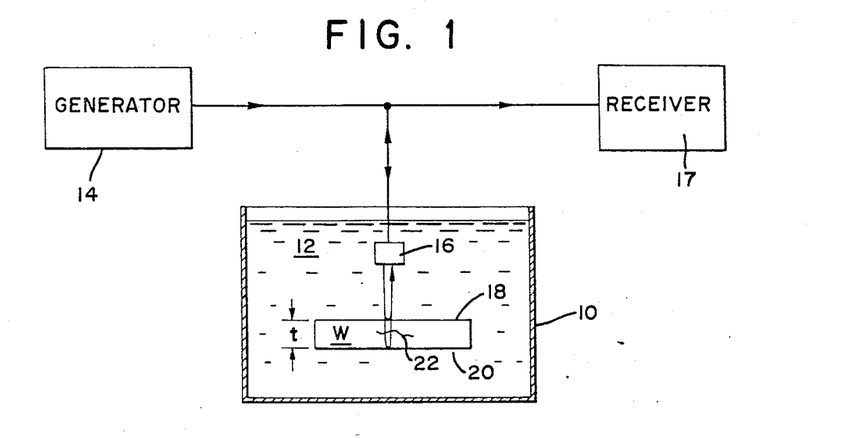
FIG. 1 is a schematic illustration of an ultrasonic pulse-echo immersion test apparatus.

Referring now to the figures and FIG. 1 in particular, a typical ultrasonic pulse-echo immersion test apparatus is shown. A workpiece W having a thickness t is immersed in a tank 10 containing a liquid couplant 12. An ultrasonic frequency electrical pulse generator 14 is coupled to an ultrasonic transmitter/receiver probe 16 and provides high frequency electrical signals to the probe 16. The probe, immersed in the liquid 12, converts the electrical signals to ultrasonic frequency compressive wave energy signals, which signals are coupled to the workpiece W by means of the couplant 12, such as water. Ultrasonic echo signals arising as the result of acoustic discontinuities in the workpiece W are coupled via the couplant 12 to the test probe 16 and transmitted to a receiver unit 17.

The intensity of the ultrasonic energy reflected from the workpiece W and received by the test probe 16 is dependent, among other variables, upon the angle of incidence of the transmitted ultrasonic energy beam into the workpiece W. In FIG. 1, when the test probe 116 is disposed to cause the angle of incidence of the transmitted ultrasonic energy beam to be normal to the workpiece entrant surface 18, the amount of reflected energy received by the test probe 16 is at a maximum. It is, therefore, desirable to maintain this alignment to assure the largest possible echo signal. It is also apparent that the energy reflected from the rear wall 20 of the workpiece will be at a maximum in case of a flat, regularly shaped workpiece W. The ratio of the intensity of the sound beam reflected from the rear wall to the intensity of the signal arising responsive to a defect 22 in the workpiece W is the value used to evaluate the magnitude and position of defect 22 in the workpiece W. Defect measurements performed in accordance with the instant principle is described generally in Section 2.2 of the book "Ultrasonic Testing of Materials" by J. and H. Krautkramer, Springer-Verlag, New York, 1969.

Figure 2:
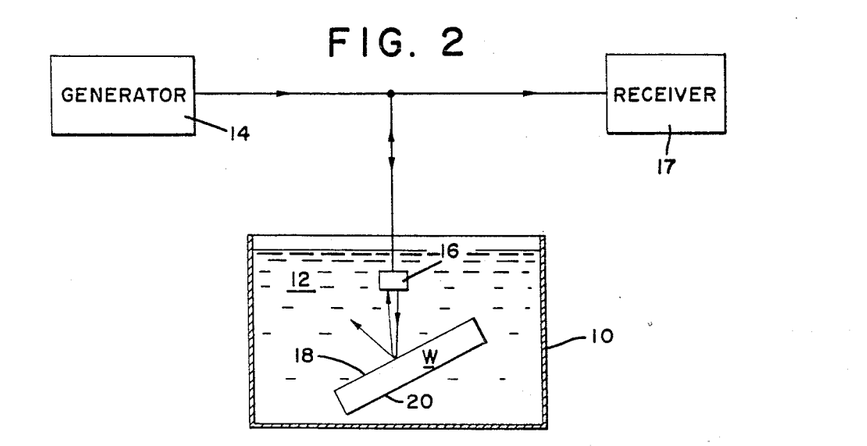
FIG. 2 is another schematic illustration of an ultrasonic pulse-echo immersion test apparatus.

If the angle of the beam axis of the test probe 16 with respect to entrant surface 18 of the workpiece W deviates from normal as shown in FIG. 2, the sound energy reflected at the entrant surface 18 and received by the test probe 16 is reduced due to the reflection and refraction of sonic energy at the entrant surface 18. In a like manner, the ultrasonic echo signal reflected from the rear wall 20 of the workpiece is also reduced. The present invention utilizes the reduced ultrasonic echo signal amplitude obtained as the result of an acute angle beam axis incidence upon the workpiece to reposition the test probe 16 for maintaining the axis of the sound beam normal to the workpiece entrant surface 18 or normal to another selected ultrasonic energy reflecting surface.

Figure 3:
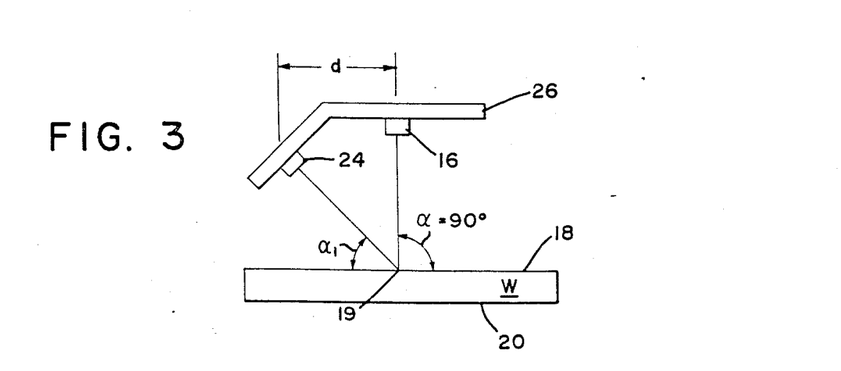
FIG. 3 is a schematic illustration of a preferred embodiment of the present invention.

In FIG. 3, an angled support 26 is shown which supports in one plane the test probe 16 for transmitting an ultrasonic energy beam into a workpiece W perpendicular to the surface and which supports an angularly disposed alignment probe 24 for transmitting an ultrasonic energy beam along a nonorthogonal path into the workpiece W. The alignment probe is disposed at a distance d from the test probe 16 and the angle between the beam axis of the alignment probe 24 and the workpiece is selected to be slightly less than 90°, preferably, being in the range from approximately 65° to 86°. Accuracy of the present alignment method increases as the angle $\alpha_1$ approaches 86°. The angle $\alpha_1$ is selected depending upon the material of the workpiece in accordance with the graphs and tables found in the Appendix of the book "Ultrasonic Testing of Materials" by J. and H. Krautkramer, Springer-Verlag, New York, 1969. The angle $\alpha_1$ is selected to cause a reflected wave intensity at a predetermined percentage of the transmitted wave intensity. When the $\alpha_1$ is only slightly less than 90°, the echo signal amplitude received by the alignment probe 24 is slightly less than the signal amplitude received by the test probe 16. The ratio of the two signals is fixed for the condition when test probe 16 is transmitting ultrasonic energy beams normal to the workpiece surface. The test probe is positioned responsive to changes of the ratio of the alignment probe echo signal amplitude to the test probe echo signal amplitude thereby maintaining the ratio at the desired fixed value.

Figure 4:
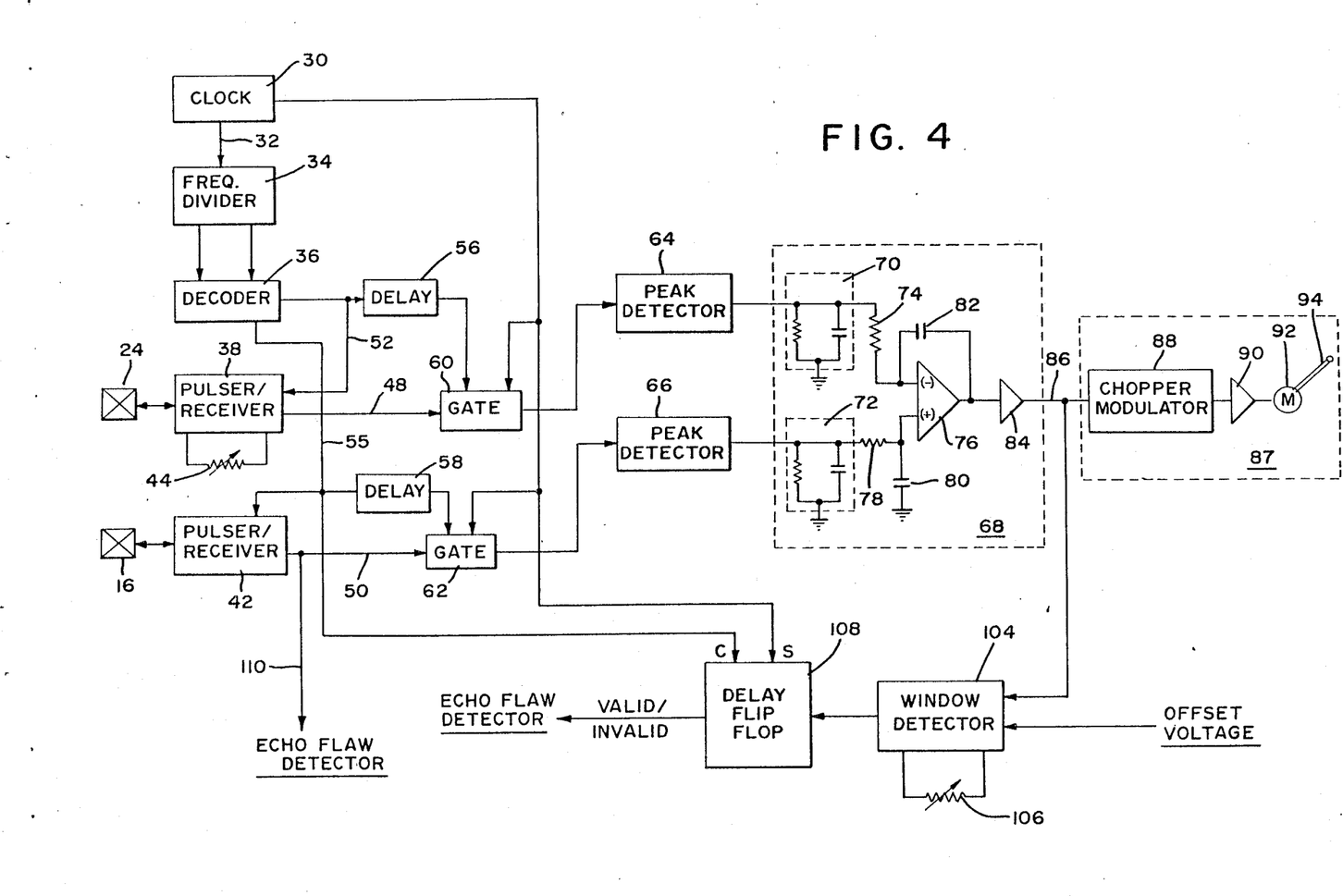
FIG. 4 is a schematic electrical circuit diagram of an electrical circuit used in conjunction with the preferred embodiment of the present invention per FIG. 3.

FIG. 4 shows a preferred embodiment of an electrical circuit used to cause the positioning of the test probe 16, FIG. 3, for providing an ultrasonic energy beam axis from the test probe 16 normal to the entrant surface 18 of the workpiece W at location 19. A clock 30 provides timing signals which are conducted along conductor 32 to a frequency divider circuit 34. The divider circuit 34 divides the clock frequency by the total number of probes in the alignment system. In the embodiment per FIG. 4, the divider 34 divides the clock frequency by a factor of two. The output of the divider 34 is the input signal to a decoder 36. The decoder 36 provides output signals to energize the pulser/receivers 38 and 42 in sequence to provide trigger signals which sequentially and cylically energize the test probe 16 and the alignment probe 24 for causing the probes to transmit and receive ultrasonic energy. The received ultrasonic energy echoes are converted by the probes to electrical signals which, after appropriate signal processing, cause the positioning of the test probe 16 as will be described hereinafter.

The pulser/receiver 38 is provided with an adjustment potentiometer 44. The potentiometer 44 is adjusted to provide the proper pulser/receiver gain so that the signal reflected from the entrant surface and received by the alignment probe 24, conducted through the pulser/receiver 38, along conductor 48 is of a predetermined smaller amplitude than the signal conducted through pulser/receiver 42 from test probe 16 along conductor 50. While the gain of either the pulser or the receiver can be adjusted, it is preferable to adjust the receiver gain. By positioning the support and hence the probes for maintaining the same amplitude difference at the output of the pulser/receivers 38 and 42, the test probe 16 will be transmitting ultrasonic energy normal to the entrant surface. By adjusting the gain of the pulser/receiver 38, the output of the pulser/receivers 38 and 42 can be made equal for the condition when test probe 16 transmits ultrasonic energy normal to the entrant surface. It is apparent that of alignment is desired at any angle other than normal to the entrant surface, for example when testing along a zig-zag path, the potentiometer 44 may be adjusted to provide the desired amplitude gain for causing the output signals of pulser/receivers 38 and 42 to be equal amplitude at any predetermined beam axis angle incident upon the entrant surface.

The decoder 36 outputs are conducted to the pulser/receivers 38 and 42 associated with the alignment probe 24 and the test probe 16 along conductors 52 and 55 respectively as well as to delay circuits 56 and 58. The output of delay circuit 56 is coupled to a gate circuit 60 to permit only signals received by alignment probe 24 during a predetermined time interval to be processed by the servo amplifier circuit 68. In a like manner, a gate circuit 62 is provided to permit only signals received by test probe 16 during a predetermined time interval to be processed by the servo amplifier circuit 68. The gate circuits 60 and 62 also receive an input signal from the clock 30 for synchronizing the gate circuit with the transmit pulse from the respective pulser/receiver circuits.

The echo signals received during the predetermined gate signal time intervals are hereinafter referred to as the gated video signals. The gated video signals are transmitted to peak detector circuits 64 and 66 respectively. The output signals of the peak detectors, the peak amplitudes of the gated video signals, are provided as input signals to the servo amplifier circuit 68. The servo amplifier circuit 68 comprises RC time constant storing circuits 70 and 72, a resistor 74 connected from RC time constant circuit 70 to the negative input of a differential amplifier 76, a resistor 78 coupled from RC time constant storing circuit 72 to capacitor 80, both the resistor 78 and capacitor 80 are connected to the positive input of the differential amplifier 76, the other terminal from capacitor 80 is coupled to ground, and feedback capacitor 82 is coupled from the output of amplifier 76 to the negative input of the amplifier 76. The output signal from differential amplifier 76 is conducted to a buffer amplifier 84 which provides an output error signal. The output error signals of the servo amplifier circuit 68 is a bipolar direct current voltage signal indicative of the angle of incidence of the ultrasonic energy transmitted from the test probe 16 to the workpiece W. The polarity of the signal is indicative of the direction in which the test probe must be rotated for transmitting ultrasonic energy at a predetermined angle to the workpiece surface. The magnitude of the error signal is indicative of the amount of rotation the test probe must undergo for transmitting ultrasonic energy at a predetermined angle to the workpiece surface.

Figure 9:
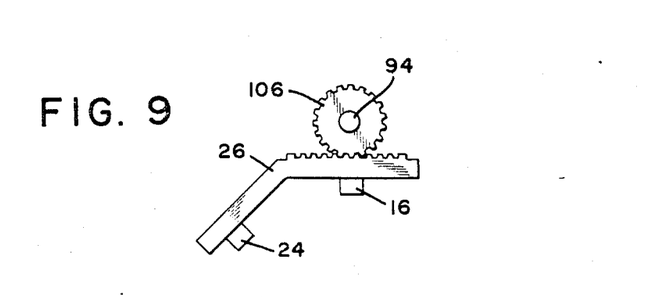
FIG. 9 is a sectional view of a portion of a preferred embodiment of the invention.

The error signal is transmitted along conductor 86 to a servomechanism system 87 which is coupled to the support 26 for rotating the support and hence the test probe to the desired position. Typical servomechanism circuits are defined and shown in the booklet "Technical Information for the Engineer", Number 1, Tenth Edition, by Singer-General Precision, Incorporated, 1969. In a preferred embodiment, the servomechanism system comprises a chopper modulator 88 which converts the direct current error signal to an alternating current signal. The output of the chopper modulator 88 is transmitted to the input of a servo amplifier 90 whose output is provided to a bidirectional motor 92. The shaft 94 of the motor is suitably coupled by means of gears to the support 26 as shown in FIG. 9, for providing rotational motion of the support responsive to the error signal.

The error signal is also transmitted to the input of a window detector circuit 104. The output of the window detector circuit 104 assumes a first logic level state when the error signal is within predetermined amplitude limits, the window, and changes to a second logic level state upon the error signal amplitude exceeding the predetermined limits. A potentiometer 106 permits adjustment of the amplitude limits. Additionally a direct current offset voltage is provided to the window detector in the case where the error signal nominal value is not zero volts. The output of the window detector is transmitted to the input of delay flip-flop 108. Upon receipt of a pulse from decoder 36, synchronous with the trigger pulse to pulser/receiver 42, the output of the delay flip-flop 108 will assume a logic level state responsive to the error signal being within or outside the amplitude limits of the window detector 104. The output of the delay flip-flop 108 is conducted to an echo flaw detector (not shown) as a "valid" or "invalid" signal. If the error signal is within the predetermined amplitude limits a valid signal is conducted to the flaw detector for providing that the ensuing echo signal received from the test probe 16 is to be measured and elevated since the test probe 16 is transmitting ultrasonic energy along the desired beam axis incident upon the entrant surface. When the error signal is outside the predetermined limits, the flaw detector receives an invalid signal and the ensuing test probe 16 echo signal is not evaluated by the flaw detector because the ultrasonic beam axis deviates from the desired angle relative to the entrant surface of the workpiece.

Figure 5:
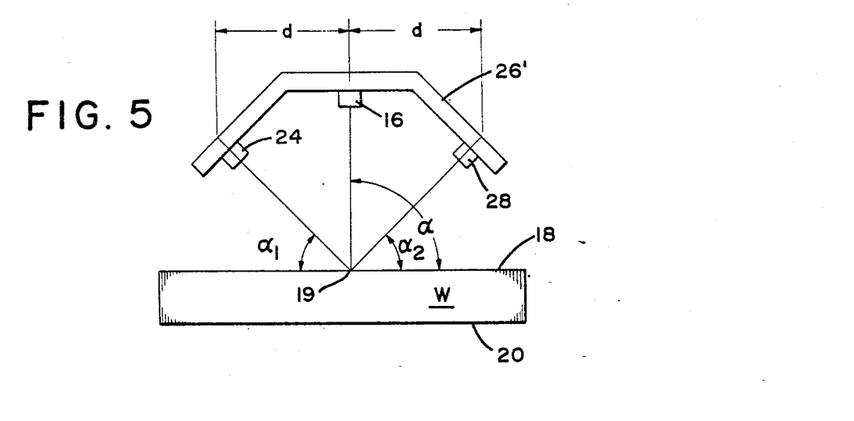
FIG. 5 is an illustration of an alternative embodiment of the present invention.

If the support 26 is provided with an additional bend and a further alignment probe 28 is affixed thereto to transmit ultrasonic energy beams into the workpiece W at an angle $\alpha_2$, in a symmetrical manner with respect to probes 16 and 24, see FIG. 5, the amplitude of the echo signal responsive to the entrant surface 18 and received by alignment probe 28 will be equal to the echo signal amplitude received by alignment probe 24 only when the angle $\alpha$ is equal to 90° and when the angle $\alpha_1$ equals angle $\alpha_2$.

It is essential for testing rough and/or highly irregular contoured surface workpieces that the test probe beam axis and the alignment probe beam axes coincide at the point 19 on the surface of the workpiece. In this case, the test probe can be positioned normal to the entrant surface of such a highly irregular contoured surface. When a smooth surface workpiece is tested, the alignment probe energy beams and the test probe energy beams need not coincide.

As will be explained hereinafter, the signals received by the alignment probes 24 and 28 are the input signals provided to an electrical circuit which is coupled to a positioning means to effect rotation of the support 26', the positioning means aligning the support 26' for causing the amplitude of the signal reflected from the entrant surface 18 at location 19 and received by the alignment probe 24 to equal the amplitude of the signal reflected at location 19 and received by the alignment probe 28. Under this condition, the angle $\alpha$ equals 90 degrees and the beam axis of the test probe 16 is normal to the entrant surface 18 at the location 19. As illustrated, the arrangement shown in FIG. 5 using a pair of alignment probes straddling the test probe 16 provides correction for the test probe 16 relative to the workpiece entrant surface 18 in the plane through the probes 24, 16 and 28.

Figure 6:
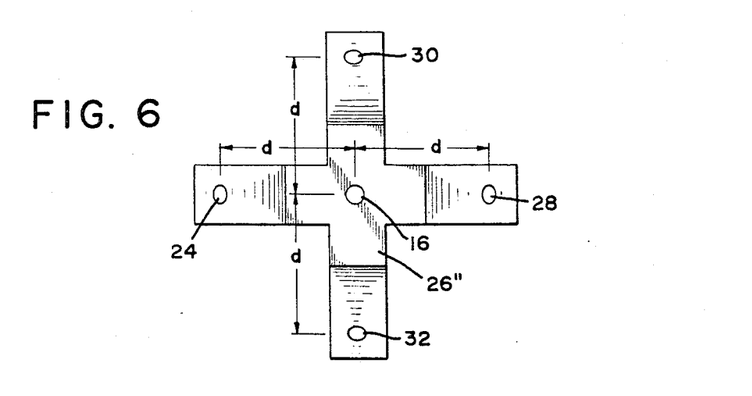
FIG. 6 is a plan view of further alternative embodiment of the present invention.

FIG. 6 depicts a cross shaped support 26 inch, comprising two of the supports shown in FIG. 5, for supporting two pairs of alignment probes 24 and 28, 30 and 32 to provide alignment information in two mutually perpendicular planes. The probes are mounted symmetrical with respect to the test probe 16 as explained heretofore. In this embodiment, the support 26 inch is mounted to means providing motion in two planes.

As a result of the geometrical position of the alignment probes, it is apparent that the oppositely disposed pairs of alignment probes 24, 28 and 30, 32 may transmit ultrasonic energy and receive ultrasonic energy to and from one another. This condition is undesirable since the angle $\alpha_1$ or $\alpha_2$ preferably is dependent upon the energy reflected from the workpiece entrant surface 18 at location 19 to the same alignment probe which transmitted the energy beam.

To prevent the undesired cross coupling of signals between the pairs of oppositely disposed alignment probes, each alignment probe is cyclically caused to transmit and receive ultrasonic energy sequentially during predetermined time intervals. Hence, only one alignment probe transmits and receives ultrasonic energy during any given time interval. The cycle is continued until all four alignment probes have transmitted and received ultrasonic energy, after which time the test probe is positioned to an orientation whereat the transmitted ultrasonic energy beam axis from test probe 16 is normal to the entrant surface 18. The signal from test probe 16 is then used to search for defects 22 within the workpiece W. The speed of such a system therefore, is one-fifth the speed of heretofore conventional systems. It should be understood that the workpiece W as shown is only an incremental portion of a larger workpiece and that the workpiece, typically, may be of irregular shape comprising curved contours and rough surfaces. If a one hundred percent inspection of the workpiecec is required and the workpiece is of such a character that it has slowly changing contours, the alignment probes need only be sequentially activated after a predetermined number of test probe pulse-echo ultrasonic tests have been performed.

Figure 7:
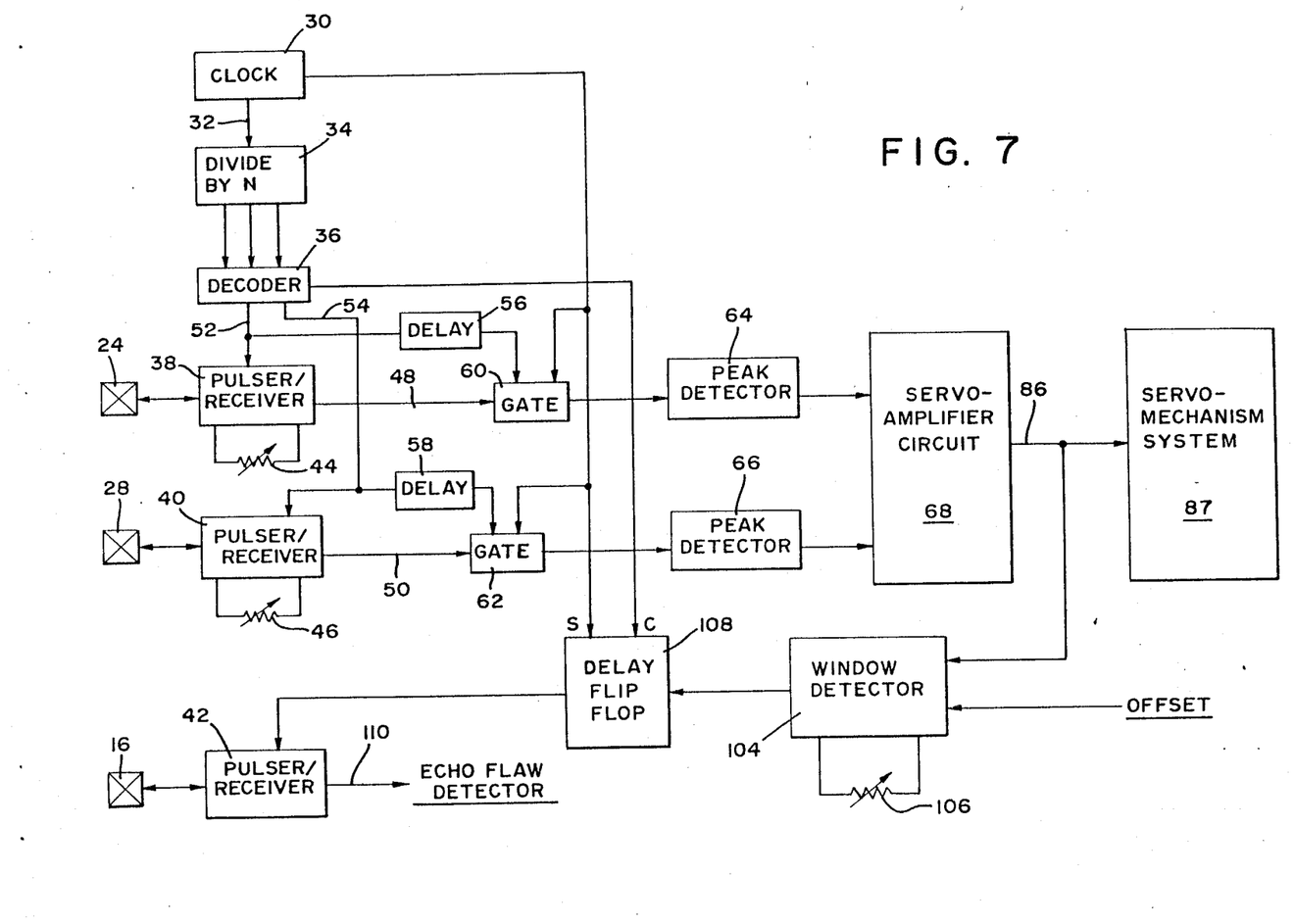
FIG. 7 is a schematic electrical circuit diagram of an electrical circuit used in conjunction with the embodiment shown in FIG. 6.
Figure 8:
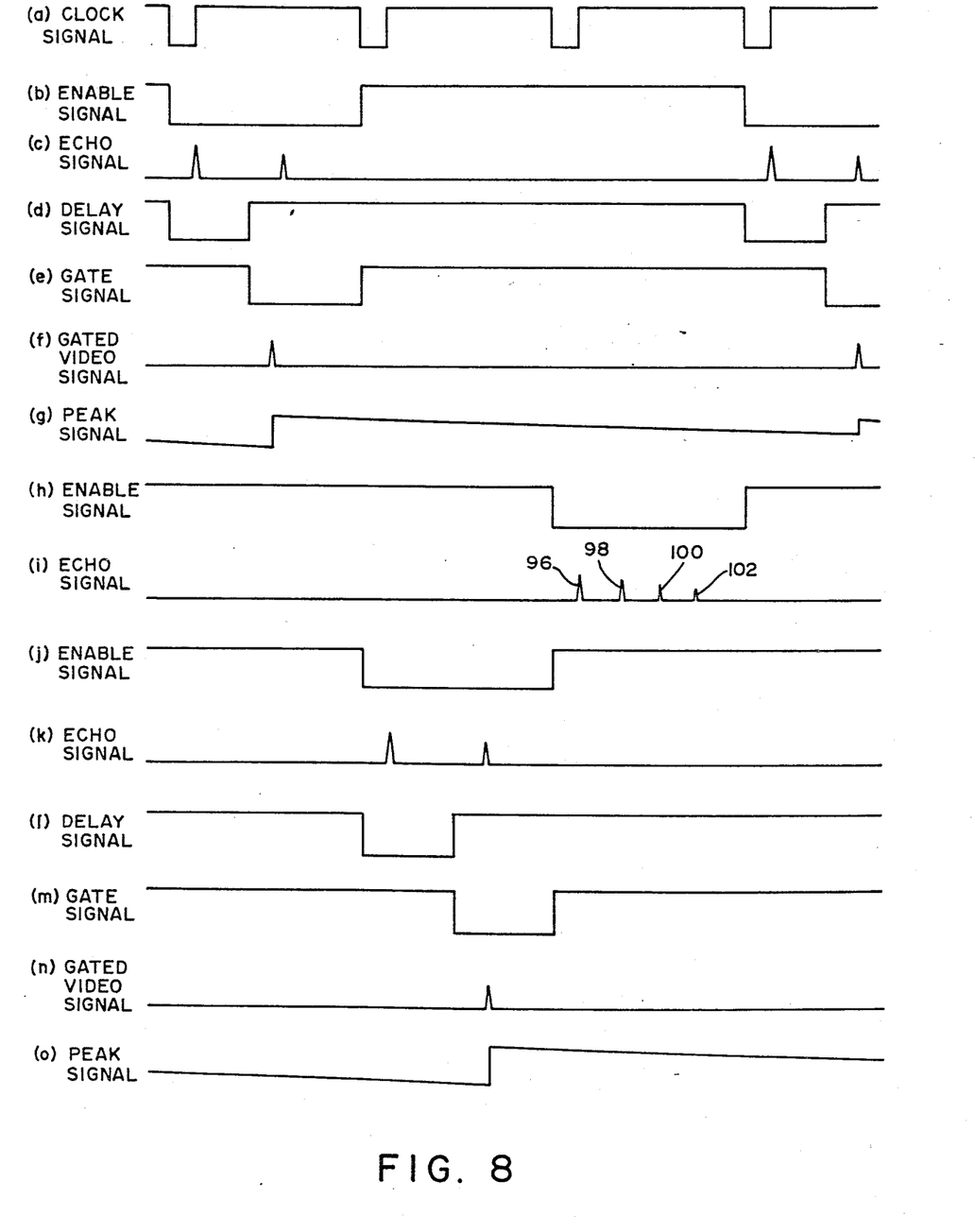
FIG. 8 is a schematic timing diagram illustrating the signals generated within the electrical circuit as shown in FIG. 6.

FIG. 7 shows an electrical circuit for causing the support 26'' per FIG. 6 to be positioned to assure that the beam axis of the ultrasonic energy from the test probe 16 is normal to the entrant surface 18 of the workpiece W at location 19. FIG. 8 is a timing diagram of the signals generated within the circuit shown in FIG. 7. A clock 30 provides timing signals for the electrical circuit and the cyclically generated signals, FIG. 8, trace a, are conducted along conductor 32 to a frequency divider circuit 34. The divider circuit 34 divides the clock frequency by the total number of probes in the alignment system. In the embodiment per FIG. 6, the divider 34 divides the clock frequency by a factor of five. In the circuit per FIG. 5, wherein the apparatus necessary for aligning a test probe 16 along one axis is shown, only three probes are used, and the divider 34 divides the clock frequency by a factor of three. The output of the divider 34 is the input signal to a decoder 36. The decoder 36 provides output signals to energize the pulser/receivers 38 and 40 in sequence to provide trigger signals which sequentially and cyclically energize the alignment probes 24 and 28 for causing the probes to transmit and receive ultrasonic energy. An additional output of the decoder 36 is transmitted to delay flip-flop 108 as a clock input. When the test probe 16 is in the desired position, a signal from the delay flip-flop energizes the test probe 16. The ultrasonic energy echoes received by the alignment probes are converted by the probes to electrical signals which after appropriate signal processing, cause the positioning of the test probe 16 as will be described hereinafer.

The pulser/receivers 38 and 40 are provided with respective adjustment potentiometers 44 and 46. The potentiometers 44 and 46 are adjusted to provide the proper pulser/receiver gain so that the signals received by the alignment probes 24 and 28, FIG. 8 traces c and k, conducted through the pulser/receivers 38 and 40, along conductors 48 and 50, are of equal amplitude when the signal received by the test probe 16 is at a maximum. At that time, the test probe 16 is transmitting ultrasonic energy into the workpiece W at location 19 in a direction normal to the workpiece entrant surface 18 as described supra. The gain adjustment provides that the alignment probes 24 and 28 need not be critically matched since adjustment of the potentiometers 44 and 46 will provide the required compensation.

The decoder 36 outputs, the enable signals shown in FIG. 8 traces b and j, are conducted to the pulser/receivers associated with the alignment probes 24 and 28 along conductors 52 and 54 respectively as well as to the delay circuits 56 and 58. The output of delay circuit 56, trace d, is coupled to a gate circuit 60 to permit only signals received by alignment probe 24 during a predetermined time interval trace e, to be processed by the servo amplifier circuit 68. In a like manner, a gate circuit 62 is provided to permit only signals received by alignment probe 28 during a predetermined time interval, trace m, to be processed by the servo amplifier circuit 68.

The echo signals received during the predetermined gate signal time intervals are hereinafter referred to as the gated video signals. These signals are shown in FIG. 8, traces f and n, and are transmitted from alignment probes 24 and alignment probe 28 respectively. The gated video signals are transmitted to peak detector circuits 64 and 66 respectively. The output signals of the peak detectors, the peak amplitudes of the gated video signals, FIG. 8, traces g and o, are provided as input signals to the servo amplifier circuit. The output error signal of the servo amplifier circuit 68 is a bipolar direct current voltage signal indicative of the angle of incidence of the ultrasonic energy transmitted from the test probe 16 to the workpiece W. The polarity of the signal is indicative of the direction in which the test probe must be rotated for transmitting ultrasonic energy normal to the workpiece surface. The magnitude of the error signal is indicative of the amount of rotation the test probe must undergo for transmitting ultrasonic energy normal to the workpiece surface.

The error signal is transmitted along conductor 86 to a servomechanism system 87 which is coupled to the support 26 inch for rotating the support and hence the test probe to the normal position in the same manner as described in conjunction with the embodiment per FIG. 4.

The error signal is also transmitted to a window detector circuit 104 which functions as explained hereinabove in connection with FIG. 4. In present embodiment, unlike the previous case, the output of the delay flip-flop can be used as a valid of invalid signal to a flaw detector, but in the preferred embodiment, the output of the delay flip-flop 108 energizes the pulser/receiver 42 associated with test probe 16 when the error signal is within the predetermined amplitude limits and the test probe is transmitting ultrasonic energy normal to the workpiece. When the probe is not in the proper position and the error signal is outside the predetermined amplitude limits, an energizing signal will not be transmitted to pulser/receiver 42. In this case, the decoder will re-energize the alignment probes 24 and 28 for providing a new error signal for positioning the test probe 16. In this manner, the window detector 104 and the delay flip-flop 108 provide a delay to test probe 16 to prevent the transmission of a test pulse until the test probe 16 is transmitting ultrasonic energy normal to the entrant surface.

While the above description is directed to adjusting the test probe 16 to transmit signals along an axis normal to the entrant surface, it is apparent that upon aligning the system when the test probe 16 is transmitting ultrasonic energy along another beam axis relative to a workpiece, the gain of pulser/receivers 38 and 40 can be adjusted by potentiometers 44 and 46 to ensure that the test probe assumes such other position.

By means of selecting the delay times of delay 56 and delay 58, the test probe 16 is aligned in a direction normal to a selected ultrasonic reflecting surface. The delay and consequently the gate signal can be made to occur during the time interval when front wall echoes, rear wall echoes, or defect responsive echoes are received, see generally trace i, FIG. 8.

After the support 26 is positioned and test probe 16 is properly aligned with respect to the workpiece W, the test probe pulser/receiver 42 is enabled by a signal from the delay flip-flop 108 (FIG. 8, trace h), the test probe 16 then transmits an ultrasonic energy signal into the workpiece to search for anomalies in the workpiece W. In the FIG. 8, trace i, the first signal 96 is the "main bang," the subsequent signals 98, 100 and 102 represent the echo from the entrant surface, an anomaly, and the rear wall respectively. The output of pulser/receiver 42 is coupled, along conductor 110, to an echo flaw detector means, as is well-known in the art, to display and record defect responsive signals.

The above embodiment uses a single test probe and a single alignment probe. If the positioning is very critical, additional alignment probes may be disposed in juxtaposition to the alignment probes 24, 28, etc.

In the above description, a multi-membered angle support is described for supporting the alignment probes. In an alternative embodiment, the probe is mounted for pivotal motion. That is, the alignment probes are pivoted about a pin to cause the ultrasonic energy beam axis transmitted from the alignment probe to be incident upon a workpiece at an angle $\alpha_1$, when the test probe beam axis is normal to the workpiece surface. In another embodiment, the alignment probes are constructed within their housings to transmit ultrasonic energy at an angle from the probe into a workpiece. In both the described alternative embodiments a straight, non-angled, support is used.

While in the circuit per FIGS. 4 and 7 an analog signal is generated at the output of servo amplifier circuit 68 for causing the repositioning if the test probe, alternatively, a digital signal may be generated. The signal is indicative of the ultrasonic energy reflecting surface and the signal is transmitted to positioning means for causing the beam axis to be normal to the desired ultrasonic energy reflecting object, i.e. the entrant surface, a defect, an interface between layers within the workpiece, the rear wall, etc.

It must be understood that while the above embodiments illustrate the method for aligning a test probe 16 along one axis, either $\theta$ or $\phi$, an identical electrical circuit is used to align the probe along the second axis. The timing is arranged to alignment anlignment of the probe along the first axis and then subsequently align the probe along the second axis.

While there have been described and illustrated certain preferred embodiments of the present invention, it will be apparent to those skilled in the art that further variations and modifications may be made without deviating from the scope of the invention which shall be limited only by the scope of the appended claims.

What is claimed is:
1. An apparatus for use in immersion pulse-echo ultrasonic testing comprising:
   transducer means comprising a test probe means and alignment determining probe means disposed in fixed spatial relationship with each other and each providing when energized and acoustically coupled to a workpiece respective ultrasonic energy beams whose axis are converging toward a point upon a workpiece to be tested and form an acute angle with respect to each other;
   means coupled to said transducer means for cyclically energizing said transducer means for causing said transducer means to transmit ultrasonic search signals toward the workpiece and receive in response thereto echo signals arising from such search signals being incident upon a selected surface of the workpiece;
   means coupled to said transducer means for receiving said echo signals and providing in response thereto an output signal commensurate with the deviation of the beam axis of said test probe from a predetermined angle of incicence upon a selected surface of the workpiece, and
   positioning means coupled to said transducer means and receiving said output signals for positioning said transducer means responsive to said output signal.

2. An apparatus for use in immersion pulse-echo ultrasonic testing as set forth in claim 1, and including a common support for supporting said test probe means and said alignment determining probe means.

3. An apparatus for use in immersion pulse-echo ultrasonic testing as set forth in claim 1, said predetermined angle of incidence being normal to said selected workpiece surface.

4. An apparatus for use in immersion pulse-echo ultrasonic testing as set forth in claim 3, said means coupled to said transducer means for receiving said echo signals including peak-detector means for obtaining the peak value of said echo signals.

5. An apparatus for use in immersion pulse-echo ultrasonic testing as set forth in claim 4, said means coupled to said transducer means for receiving said echo signals further including delay means for causing echo signals received during a predetermined time interval to be conducted to said peak-detector means.

6. An apparatus for use in immersion pulse-echo ultrasonic testing as set forth in claim 4, said means coupled to said transducer means further including comparator means for comparing said peak value of said echo signals and providing a second output signal indicative of the difference of said peak value signals.

7. An apparatus for use in immersion pulse-echo ultrasonic testing as set forth in claim 6, said second output signal being conducted to servomechanism means coupled for positioning said transducer means for causing said test probe means to transmit ultrasonic search signals along said predetermined angle of incidence to said selected workpiece surface.

8. An apparatus for use in immersion pulse-echo ultrasonic testing as set forth in claim 6, said means coupled to said transducer means for receiving said echo signals further including delay means for causing a signal to be provided from the test probe means to defect evaluation means only after said test probe means is positioned for transmitting ultrasonic search signals along said predetermined angle.

9. An apparatus for use in immersion pulse-echo ultrasonic testing as set forth in claim 1, said selected surface is the entrant surface of the workpiece.

10. An apparatus for use in immersion pulse-echo ultrasonic testing comprising:

transducer means comprising a test probe means and alignment determining probe means disposed in fixed spatial relationship with each other and each providing when energized and acoustically coupled to a workpiece respective ultrasonic energy beams whose axes are converging toward a point upon a workpiece to be tested and form an acute angle with respect to each other;

first means coupled to said transducer means for causing said alignment determining probe means to be cyclically energized for transmitting ultrasonic search signals toward the workpiece and to receive in response to said search signals echo signals arising from such search signals being incident upon the workpiece;

second means coupled to said alignment determining probe means for providing in response to said echo signals an output signal commensurate with the deviation of the beam axis of said test probe means from predetermined angle of incidence upon a selected surface of the workpiece, and positioning means coupled to said transducer means and receiving said output signal for positioning said transducer means responsive to said output signal.

11. An apparatus for use in immersion pulse-echo ultrasonic testing as set forth in claim 10, said predetermined angle of incidence being normal to said selected surface of the workpiece.

12. An apparatus for use in immersion pulse-echo ultrasonic testing as set forth in claim 11, said second means coupled to said alignment determining probe means including peak-detector means for obtaining the peak value of said echo signals.

13. An apparatus for use in immersion pulse-echo ultrasonic testing as set forth in claim 12, said second means coupled to said alignment determining probe means further including delay means for causing echo signals received during a predetermined time interval to be conducted to said peak-detector means.

14. An apparatus for use in immersion pulse-echo ultrasonic testing as set forth in claim 12, said second means including comparator means coupled for receiving and comparing said peak value signals and providing a second output signal indicative of the difference of said peak value signals.

15. An apparatus for use in immersion pulse-echo ultrasonic testing as set forth in claim 14, said second output signal being conducted to servomechanism means forming a part of said positioning means.

16. An apparatus for use in immersion pulse-echo ultrasonic testing as set forth in claim 14, and said second means further including delay means for causing a defect responsive signal from said test probe means responsive to said peak values being of substantially equal amplitude.

17. An apparatus for use in immersion pulse-echo ultrasonic testing as set forth in claim 10, said selected surface is the entrant surface of the workpiece.

* * * * *